(12) United States Patent
Inoue et al.

(10) Patent No.: US 11,071,933 B2
(45) Date of Patent: Jul. 27, 2021

(54) FILTER AND AIR-CONDITIONING DEVICE

(71) Applicant: Murata Manufacturing Co., Ltd., Nagaokakyo (JP)

(72) Inventors: Takafumi Inoue, Nagaokakyo (JP); Kenichiro Takumi, Nagaokakyo (JP); Daiji Tamakura, Nagaokakyo (JP); Masamichi Ando, Nagaokakyo (JP)

(73) Assignee: MURATA MANUFACTURING CO., LTD., Nagaokakyo (JP)

(*) Notice: Subject to any disclaimer, the term of this patent is extended or adjusted under 35 U.S.C. 154(b) by 0 days.

(21) Appl. No.: 16/884,721

(22) Filed: May 27, 2020

(65) Prior Publication Data

US 2020/0282350 A1  Sep. 10, 2020

Related U.S. Application Data

(63) Continuation of application No. 16/512,585, filed on Jul. 16, 2019, now Pat. No. 10,710,011, which is a continuation of application No. PCT/JP2018/035924, filed on Sep. 27, 2018.

(30) Foreign Application Priority Data

Oct. 17, 2017 (JP) .............................. JP2017-201241
Mar. 28, 2018 (JP) .............................. JP2018-062193

(51) Int. Cl.
*B01D 39/08* (2006.01)
*D02G 3/44* (2006.01)
*H01L 41/08* (2006.01)

(52) U.S. Cl.
CPC ............. *B01D 39/08* (2013.01); *D02G 3/449* (2013.01); *H01L 41/082* (2013.01); *D10B 2401/13* (2013.01); *D10B 2401/16* (2013.01)

(58) Field of Classification Search
CPC ............ D10B 2401/13; D10B 2401/16; H01L 41/082; B01D 39/08; D02G 3/449
See application file for complete search history.

(56) References Cited

U.S. PATENT DOCUMENTS

| 6,567,595 B1* | 5/2003 | Nishimura | G02B 6/29377 385/123 |
| 10,536,779 B2 | 1/2020 | Kitamura et al. | |
| 2002/0041746 A1* | 4/2002 | Kato | G02B 6/03644 385/123 |

(Continued)

FOREIGN PATENT DOCUMENTS

| JP | 2006320491 A | 11/2006 |
| JP | 2011194336 A | 10/2011 |

(Continued)

OTHER PUBLICATIONS

International Search Report issued for PCT/JP2018/035924, dated Dec. 18, 2018.

(Continued)

*Primary Examiner* — Anthony R Shumate
(74) *Attorney, Agent, or Firm* — Arent Fox LLP

(57) ABSTRACT

An antibacterial mask that includes a filter portion having a first principal surface and a second principal surface opposite the first principal surface, the filter portion including a plurality of first piezoelectric yarns that generate at least a first charge by stretching.

30 Claims, 15 Drawing Sheets

(56) References Cited

U.S. PATENT DOCUMENTS

| | | | |
|---|---|---|---|
| 2004/0247270 A1* | 12/2004 | Okuno | G02B 6/02004 385/123 |
| 2011/0083686 A1* | 4/2011 | Yang | A24D 3/163 131/328 |
| 2011/0260584 A1* | 10/2011 | Yu | H01L 41/082 310/339 |
| 2012/0214040 A1* | 8/2012 | Tsutsumi | H01M 4/0409 429/99 |
| 2013/0273402 A1* | 10/2013 | Tsutsumi | H01M 10/36 429/99 |
| 2013/0291878 A1 | 11/2013 | Takayama et al. | |
| 2014/0049137 A1 | 2/2014 | Ando et al. | |
| 2015/0280102 A1* | 10/2015 | Tajitsu | G01L 1/16 310/338 |
| 2016/0190427 A1 | 6/2016 | Kim et al. | |
| 2016/0274306 A1* | 9/2016 | Yukawa | G02F 1/37 |
| 2017/0029985 A1* | 2/2017 | Tajitsu | H04R 17/005 |
| 2017/0331027 A1* | 11/2017 | Kim | H01L 41/193 |
| 2018/0108826 A1* | 4/2018 | Tajitsu | D03D 1/0088 |
| 2018/0240959 A1 | 8/2018 | Kim et al. | |
| 2018/0355525 A1 | 12/2018 | Ando et al. | |
| 2019/0003905 A1 | 1/2019 | Yoshida et al. | |
| 2019/0008687 A1 | 1/2019 | Ishiura et al. | |
| 2019/0038787 A1* | 2/2019 | Ando | H01L 41/113 |
| 2019/0273199 A1 | 9/2019 | Tajitsu et al. | |
| 2019/0330771 A1 | 10/2019 | Takumi et al. | |

FOREIGN PATENT DOCUMENTS

| | | |
|---|---|---|
| JP | 2017183432 A | 10/2017 |
| JP | 2002203996 A | 7/2019 |
| WO | 2015159832 A1 | 10/2011 |
| WO | 2012091087 A1 | 7/2012 |
| WO | 2016175321 A | 11/2016 |
| WO | 2017111108 A1 | 6/2017 |

OTHER PUBLICATIONS

Fukada, E.; "Piezoelectricity of Biopolymers", Polymer vol. 16 (1967), No. 9, pp. 795-800. (Translation of abstract only).

Takaki, Koichi; "Agricultural and Food Processing Applications of High-Voltage and Plasma Technologies"; J. HTSJ, vol. 51, No. 216, Jul. 2012, pp. 64-69. (Translation of Section 5 p. 67 "Freshness retention and component extraction by high voltage").

Microorganism Control—Science and Engineering published by Kodansha Ltd, Copyright T. Tsuchido, H. Kourai, H. Matsuoka, J. Koizumi, 2002; "Electrical Control" Section 4.1.3, p. 50. (Translation of section 4.1.3, p. 50).

Written Opinion of the International Searching Authority issued for PCT/JP2018/035924, dated Dec. 18, 2018.

* cited by examiner

FILTER AND AIR-CONDITIONING DEVICE

CROSS REFERENCE TO RELATED APPLICATIONS

The present application is a continuation of application Ser. No. 16/512,585, filed Jul. 16, 2019, which is a continuation of International application No. PCT/JP2018/035924, filed Sep. 27, 2018, which claims priority to Japanese Patent Application No. 2017-201241, filed Oct. 17, 2017, and Japanese Patent Application No. 2018-062193, filed Mar. 28, 2018, the entire contents of each of which are incorporated herein by reference.

FIELD OF THE INVENTION

One embodiment of the present invention relates to a filter and an air-conditioning device.

BACKGROUND OF THE INVENTION

Conventionally, many proposals have been made on antibacterial filters (see Patent Document 1). The mask filter disclosed in Patent Document 1 is made by applying a viscous agent to a meshed fabric having mesh openings which open through the thickness, adding adhesive force to the meshed fabric, and attracting activated charcoal particles to the meshed fabric to which the adhesive force is added.

Patent Document 1: Japanese Patent Application Laid-Open No. 2006-320491

SUMMARY OF THE INVENTION

The mask filter disclosed in Patent Document 1 still needs to be improved in terms of removal of fine particles such as dust or bacteria.

Therefore, an object of one embodiment of the present invention is to provide a filter and an air-conditioning device capable of effectively removing fine particles.

The filter according to one embodiment of the present invention includes a plurality of fibers arranged to form a first principal surface and a second principal surface opposite to the first principal surface, and, of the plurality of fibers, a plurality of first piezoelectric fibers that generate negative charges by stretching are arranged at least on a side of the first principal surface.

The filter according to one embodiment of the present invention generates a negative charge on the side of the first principal surface when stretched in use. In general, germs and fungi are negatively charged. Therefore, the filter can rebound germs and fungi coming close to the side of the first principal surface. In addition, the filter can attract and capture positively charged fine particles. Thus, it is possible to prevent the germs and fungi from entering into the filter. The piezoelectric fibers according to one embodiment of the present invention may include at least one of a plurality of first piezoelectric fibers that generate negative charges and a plurality of second piezoelectric fibers that generate positive charges.

Conventionally, there has been known that an electric field can inhibit the growth of germs and fungi (see, for example, "Biseibutsu Seigyo—Kagaku to Kougaku" (microbiological control—science and engineering) authored by Testuaki TSUCHIDO, Hiroki KOURAI, Hideaki MATSUOKA, and Junichi KOIZUMI, published by Kodansha Scientific. See also, for example, "Agricultural and Food Processing Applications of High-Voltage and Plasma Technologies" written by Koichi TAKAKI, J. HTSJ, Vol. 51, No. 216). A potential which produces the electric field may cause an electric current to flow in a current path formed due to humidity or the like, or in a circuit formed through a local phenomenon of microdischarge. It is considered that the electric current may weaken bacteria themselves and inhibit the growth of bacteria. The filter according to one embodiment of the present invention may include a plurality of first piezoelectric fibers that generate negative charges by stretching, so that an electric field is produced between the fibers, or when it comes close to an object having a given potential (including a ground potential) of a human body or the like. Alternatively, the plurality of first piezoelectric fibers allow an electric current to flow through moisture such as sweat between the fibers, or when they come close to an object having a given potential (including a ground potential) of a human body or the like.

Accordingly, in the filter according to one embodiment of the present invention, the plurality of first piezoelectric fibers exhibit an antibacterial effect by the following reasons. Therefore, cell membranes of bacteria or an electron transfer system for maintaining bacteria life are damaged to thereby kill bacteria or weaken bacteria themselves, due to a direct action of the electric field or current that is produced when applied to an object (clothes, footwear, or medical articles such as a mask) used by being brought close to an object having a given potential, such as a human body. Further, the electric field or current may convert oxygen contained in moisture into active oxygen species, or stress environment caused by the presence of the electric field or current may produce oxygen radicals in cells of bacteria. The action of the active oxygen species including these radicals can kill or weaken bacteria. In addition, an antibacterial effect may be produced in combination of the above reasons. The term "antibacterial" used in the present invention may include both an effect of inhibiting the generation of bacteria and an effect of killing bacteria.

Further, since a piezoelectric body is used, an electric field is produced by a piezoelectric effect, so that no power supply is required, and an electric shock may not occur. The life of the piezoelectric body lasts longer than the antibacterial effect of chemicals or the like. Further, the piezoelectric body may cause an allergic reaction less than chemicals.

The filter according to a second embodiment of the present invention includes a plurality of fibers arranged to form a first principal surface and a second principal surface opposite to the first principal surface, and, of the plurality of fibers, a plurality of second piezoelectric fibers that generate positive charges by stretching are arranged at least on the side of the second principal surface.

The filter according to second embodiment of the present invention generates a positive charge on the side of the second principal surface when stretched in use. Therefore, the filter can attract germs and fungi coming close to the side of the second principal surface. In addition, the filter can rebound positively charged fine particles. Thus, it is possible to prevent the germs and fungi from entering into the filter.

The air-conditioning device according to an embodiment of the present invention includes the filter, an inlet port, an exhaust port, and a communicating passage that communicates between the inlet port and the exhaust port, in which the filter is arranged in the communicating passage.

Since the air-conditioning device according to an embodiment of the present invention includes the filter, it can attract fine particles such as pollen or yellow dust.

According to the present invention, a filter and an air-conditioning device capable of effectively removing fine particles can be achieved.

DETAILED DESCRIPTION OF THE INVENTION

Figure 1A:
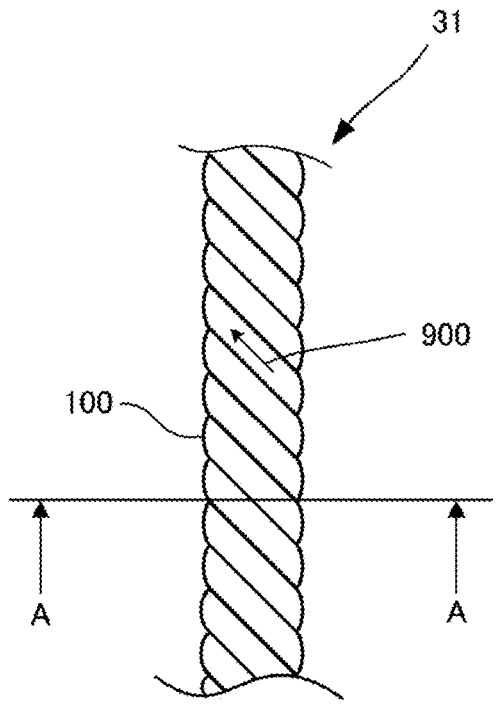
FIG. 1(A) is a view showing a configuration of a first piezoelectric fiber.
Figure 1C:
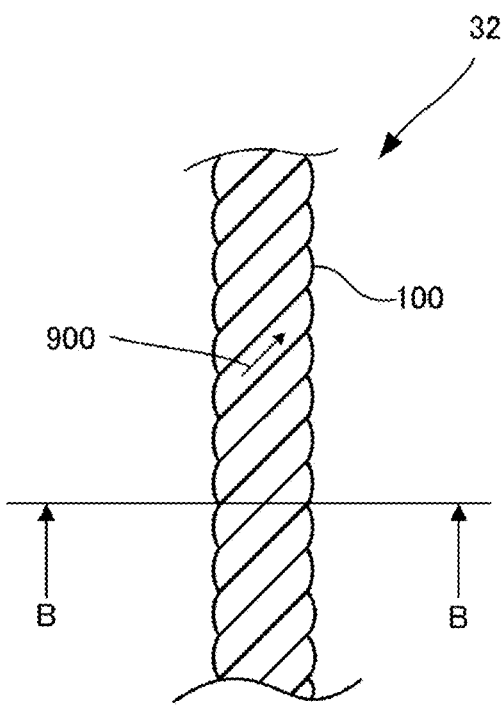
FIG. 1(C) is a view showing a configuration of a second piezoelectric fiber.
Figure 1B:
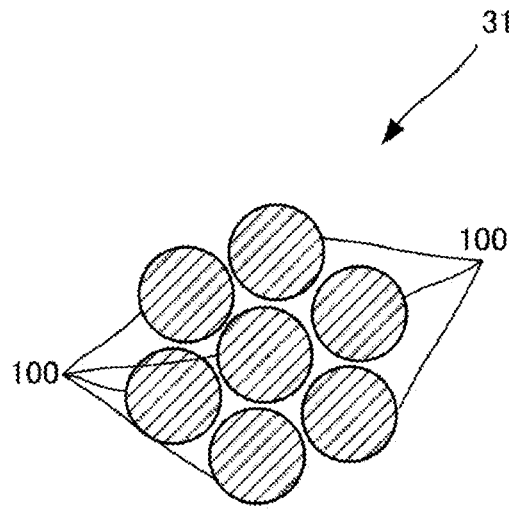
FIG. 1(B) is a cross-sectional view taken along the line A-A in FIG. 1(A)
Figure 1D:
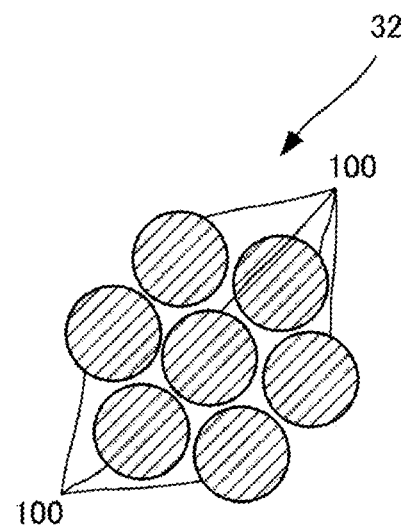
FIG. 1(D) is a cross-sectional view taken along the line B-B in FIG. 1(C).

FIG. 1(A) is a view showing a configuration of a first piezoelectric fiber, FIG. 1(B) is a cross-sectional view taken along the line A-A in FIG. 1(A), FIG. 1(C) is a view showing a configuration of a second piezoelectric fiber, and FIG. 1(D) is a cross-sectional view taken along the line B-B in FIG. 1(C). FIGS. 1(A) to 1(D) show a piezoelectric fiber obtained by twisting seven piezoelectric yarns 100 as an example. The number of piezoelectric yarns 100, however, is not limited thereto, and, in practice, it is properly set considering the uses of the yarn. The piezoelectric fiber is not limited to a fiber obtained by twisting a plurality of piezoelectric yarns, and may be a covered yarn obtained by winding a piezoelectric film around a space for a core yarn or an axial core. Further, for convenience of description, piezoelectric fibers that form a filter and piezoelectric yarns that form a piezoelectric fiber will be described first, and the filter will then be described.

The piezoelectric yarn 100 is an example of the piezoelectric fiber (electric charge generating yarn) that generates an electric charge by stretching. The piezoelectric yarn 100 is made of a functional polymer, for example, a piezoelectric polymer. Examples of the piezoelectric polymer include polylactic acid (PLA). Polylactic acid (PLA) is a piezoelectric polymer not having pyroelectricity. Polylactic acid is uniaxially stretched to have piezoelectric properties. Polylactic acid includes PLLA in which an L-form monomer is polymerized, and PDLA in which a D-form monomer is polymerized. The piezoelectric yarn 100 may further include polymers other than the functional polymer as long as it does not impair the function of the functional polymer.

Polylactic acid is a chiral polymer and has a spiral structure in its main chain. The polylactic acid exhibits piezoelectric properties when molecules are oriented by uniaxially stretching. Further, when heat treatment is applied to the polylactic acid to enhance its crystallinity, the polylactic acid has an increased piezoelectric constant. The piezoelectric yarn 100 made of uniaxially stretched polylactic acid has $d_{14}$ and $d_{25}$ tensor components as piezoelectric strain constants when the thickness direction of the piezoelectric yarn 100 is defined as a first axis, a stretching direction 900 thereof is defined as a third axis, and a direction perpendicular to both the first and third axes is defined as a second axis. Accordingly, polylactic acid most efficiently generates an electric charge when a strain occurs in a direction at an angle of 45° to the uniaxially stretching direction.

Figure 2A:
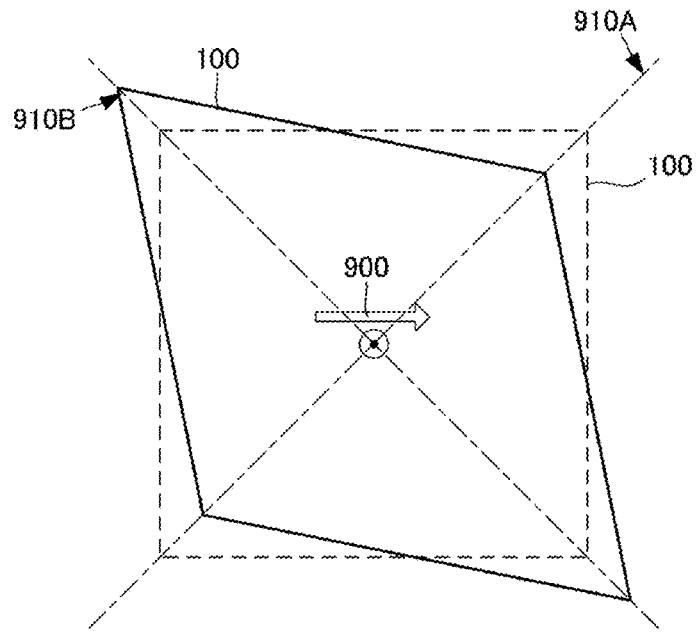
FIG. 2(A) and FIG. 2(B) are views showing a relationship of a uniaxially stretching direction of polylactic acid, an electric field direction, and deformation of a piezoelectric yarn.
Figure 2B:
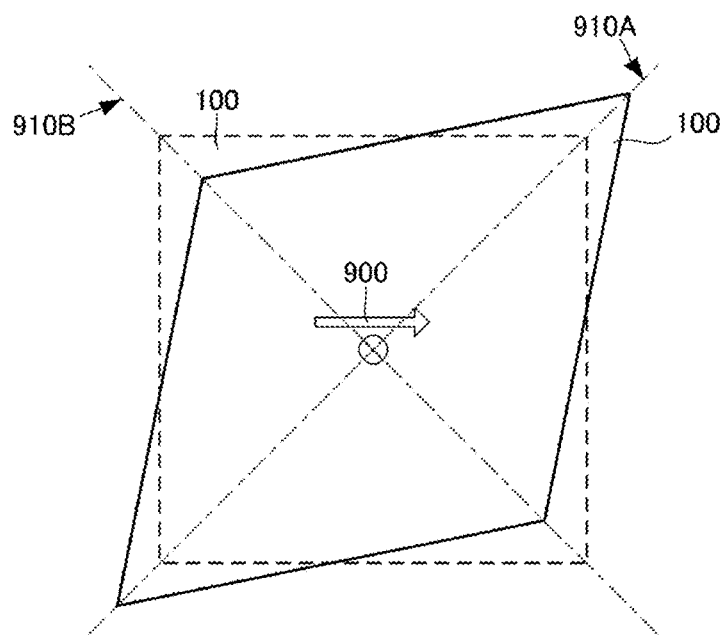

FIG. 2(A) and FIG. 2(B) are views showing a relationship of a uniaxially stretching direction of polylactic acid, an electric field direction, and deformation of the piezoelectric yarn 100. As shown in FIG. 2(A), when the piezoelectric yarn 100 shrinks in a direction of a first diagonal line 910A and stretches in a direction of a second diagonal line 910B perpendicular to the first diagonal line 910A, an electric field is produced in a direction from the back plane to the front plane of the paper. That is, the piezoelectric yarn 100 generates a negative charge on the front side of the paper plane. As shown in FIG. 2(B), even when the piezoelectric yarn 100 stretches in the first diagonal line 910A and shrinks in the second diagonal line 910B, an electric charge is generated, but the polarity is reversed, and an electric field is produced in a direction from the front plane to the back plane of the paper. That is, the piezoelectric yarn 100 generates a positive charge on the front side of the paper plane.

Since polylactic acid generates the piezoelectric properties due to molecular orientation processing by stretching, it does not need to be subjected to polling processing as other piezoelectric polymers such as PVDF or piezoelectric ceramic. The uniaxially-stretched polylactic acid has a piezoelectric constant of approximately 5 to 30 pC/N, which is an extremely high piezoelectric constant among polymers. Further, the piezoelectric constant of the polylactic acid does not vary with time and is extremely stable.

The piezoelectric yarn 100 is a fiber having a circular cross section. The piezoelectric yarn 100 is manufactured, for example, by a method of extruding a piezoelectric polymer to form a fiber; a method of melt-spinning a piezoelectric polymer to form a fiber (including, for example, a spinning and stretching method of separately performing a spinning step and a stretching step; a direct stretching method performed in combination with a spinning step and a stretching step; a POY-DTY method capable of simultaneously performing a false-twisting step; or an ultra high-speed prevention method to increase speed; and the like); a method of dry-spinning or wet-spinning a piezoelectric polymer (including, for example, a phase separation method or a dry-wet spinning method for forming a fiber by melting a polymer as a raw material in a solvent and extruding the polymer from a nozzle; a gel-spinning method for forming a fiber by uniformly rendering the polymer into gel form with a solvent contained; a liquid crystal spinning method for forming a fiber by using a liquid crystal solution or a melted body; and the like) to form a fiber; a method of electrostatic spinning a piezoelectric polymer to form a fiber; or the like. The cross sectional shape of the piezoelectric yarn 100 is not limited to a circle.

A first piezoelectric fiber 31 and a second piezoelectric fiber 32 form such a yarn (multifilament yarn) obtained by twisting a plurality of PLLA piezoelectric yarns 100. The first piezoelectric fiber 31 is a right-twisted yarn (hereinafter referred to as an S yarn) obtained by twisting the piezoelectric yarn 100 to the right. The second piezoelectric fiber 32 is a left-twisted yarn (hereinafter referred to as a Z yarn) obtained by twisting the piezoelectric yarn 100 to the left.

The stretching directions 900 of the respective piezoelectric yarns 100 are in line with the axial directions of the piezoelectric yarns 100. In the first piezoelectric fiber 31, the stretching direction 900 of the piezoelectric yarn 100 is angled leftward with respect to the axial direction of the first piezoelectric fiber 31. In the second piezoelectric fiber 32, the stretching direction 900 of the piezoelectric yarn 100 is angled rightward with respect to the axial direction of the second piezoelectric fiber 32. The inclination angle of the stretching direction 900 with respect to the axial direction of the first piezoelectric fiber 31 or the second piezoelectric fiber 32 depends on the number of twists of the first piezoelectric fiber 31 or the second piezoelectric fiber 32. Therefore, the first piezoelectric fiber 31 and the second piezoelectric fiber 32 can adjust the inclination angles of the piezoelectric yarns 100 with respect to the axial directions of the first piezoelectric fiber 31 and the second piezoelectric fiber 32 by adjusting the number of twists thereof.

Figure 3A:
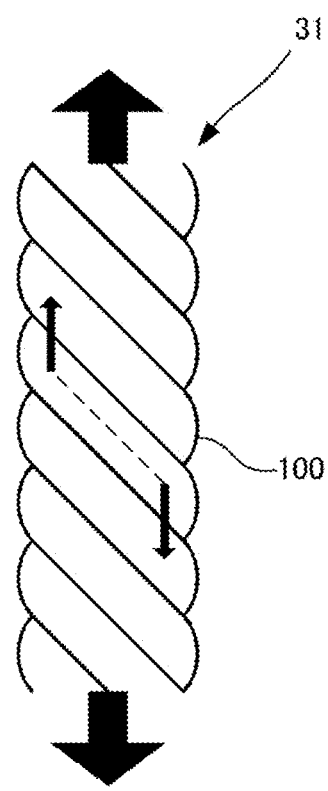
FIG. 3(A) illustrates shear stress generated in the piezoelectric fibers when a tension is applied to the first piezoelectric fibers.
Figure 3B:
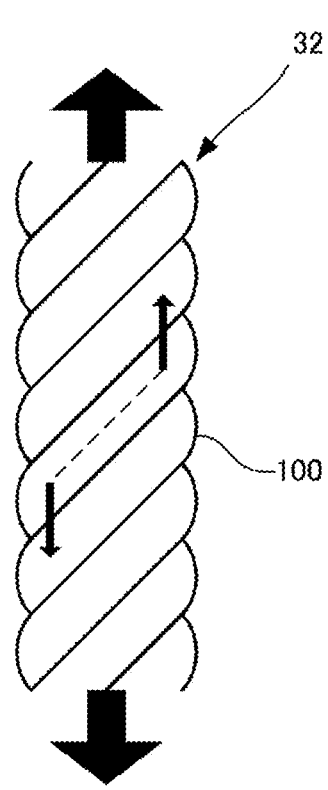
FIG. 3(B) illustrates shear stress generated in the piezoelectric fibers when a tension is applied to the second piezoelectric fibers.

FIG. 3(A) illustrates shear stress generated in the piezoelectric fibers when a tension is applied to the first piezoelectric fibers, and FIG. 3(B) illustrates shear stress generated in the piezoelectric fibers when a tension is applied to the second piezoelectric fibers.

As shown in FIG. 3(A), in the case where a tension is applied to the first piezoelectric fiber 31 of the S yarn, the surface of the first piezoelectric fiber 31 becomes such a state as shown in FIG. 2(A). This generates a negative charge on the surface of the first piezoelectric fiber 31 and a positive charge inside thereof. On the other hand, as shown in FIG. 3(B), in the case where a tension is applied to the second piezoelectric fiber 32 of the Z yarn, the surface of the second piezoelectric fiber 32 becomes such a state as shown in FIG. 2(B). This generates a positive charge on the surface of the second piezoelectric fiber 32 and a negative charge inside thereof.

Each of the first piezoelectric fiber 31 and the second piezoelectric fiber 32 produces an electric field due to the potential difference generated by these electric charges. The electric field leaks to adjacent spaces to form an electric field associated with other portions. When the potential produced in the first piezoelectric fiber 31 or the second piezoelectric fiber 32 comes close to an object having a given potential adjacent thereto, for example, a given potential (including a ground potential) of a human body or the like, an electric field is produced between the first piezoelectric fiber 31 or the second piezoelectric fiber 32 and the object.

Conventionally, there has been known that an electric field can inhibit the growth of germs and fungi (see, for example, "Biseibutsu Seigyo—Kagaku to Kougaku" (microbiological control—science and engineering) authored by Testuaki TSUCHIDO, Hiroki KOURAI, Hideaki MATSUOKA, and Junichi KOIZUMI, published by Kodansha Scientific. See also, for example, "Agricultural and Food Processing Applications of High-Voltage and Plasma Technologies" written by Koichi TAKAKI, J. HTSJ, Vol. 51, No. 216). A potential which produces the electric field may cause an electric current to flow in a current path formed due to humidity or the like, or in a circuit formed through a local phenomenon of microdischarge. It is considered that the electric current may weaken bacteria themselves and inhibit the growth of bacteria. The bacteria as used in this embodiment include germs, fungi, or microorganism such as mites or fleas.

Therefore, the first piezoelectric fiber 31 directly exerts an antibacterial effect due to the electric field formed near the first piezoelectric fiber 31 or the electric field generated when the first piezoelectric fiber 31 comes close to an object having a given potential of a human body or the like. Alternatively, the first piezoelectric fiber 31 allows an electric current to flow through moisture such as sweat, when it comes close to an object having a given potential of another adjacent fiber, a human body, or the like. The first piezoelectric fiber 31 may also directly exert an antibacterial effect due to such an electric current. Alternatively, the first piezoelectric fiber 31 may indirectly exert an antibacterial effect due to active oxygen species which oxygen contained in moisture is converted into by the action of an electric current or a voltage, radical species generated by the interaction with an additive contained in the fibers or catalysis, or other antibacterial species (amine derivatives or the like). Alternatively, stress environment caused by the presence of the electric field or current may produce oxygen radicals in cells of bacteria. This may allow the first piezoelectric fiber 31 to indirectly exert an antibacterial effect. In addition, the second piezoelectric fiber 32 can also directly or indirectly exert an antibacterial effect in the same manner as the first piezoelectric fiber 31. As the radical, superoxide anion radical (active oxygen) or hydroxyl radical may be generated. The term "antibacterial" used in this embodiment may include both an effect of inhibiting the generation of bacteria and an effect of killing bacteria.

Figure 4A:
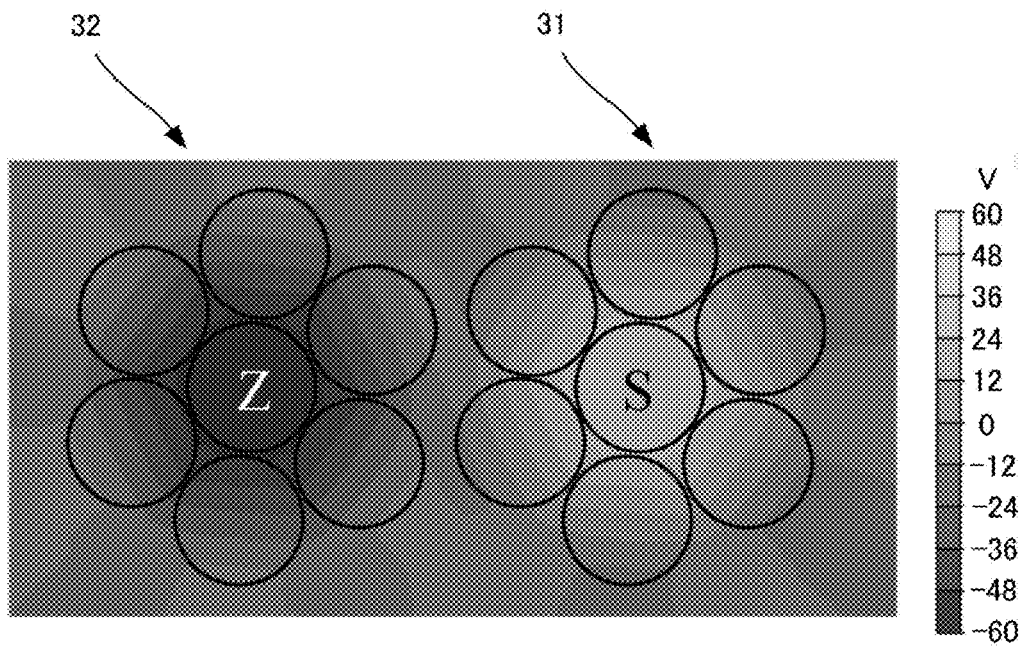
FIG. 4(A) is a view showing potentials in the first piezoelectric fiber and the second piezoelectric fiber.
Figure 4B:
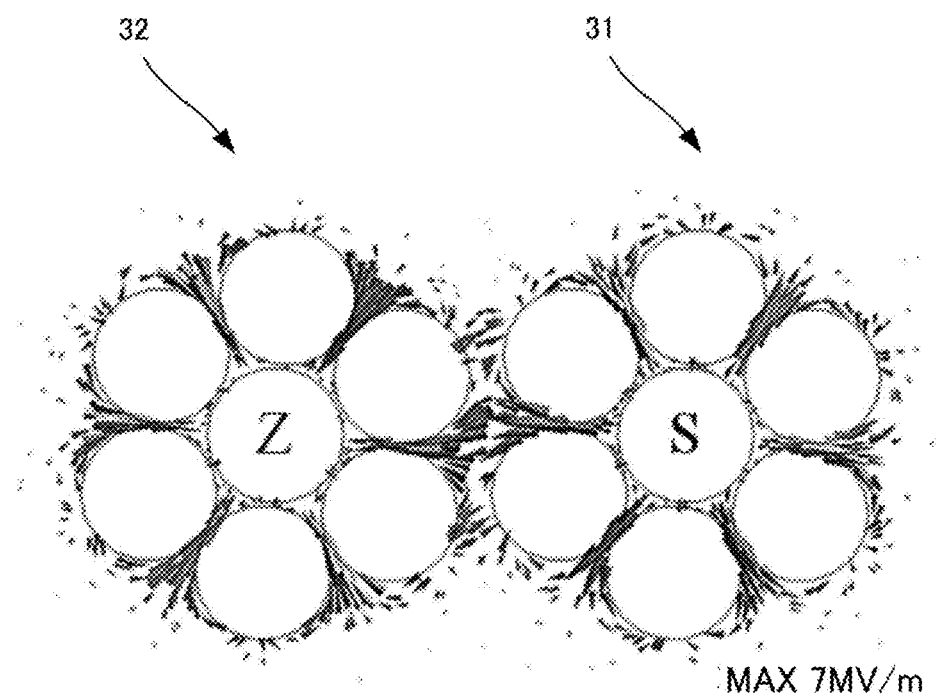
FIG. 4(B) is a view showing an electric field.

FIG. 4(A) is a view showing potentials in the first piezoelectric fiber and the second piezoelectric fiber, and FIG. 4(B) is a view showing an electric field. FIGS. 4(A) and 4(B) show a piezoelectric fiber obtained by twisting seven piezoelectric yarns as an example.

In the case where the first piezoelectric fiber 31 (S yarn) and the second piezoelectric fiber 32 (Z yarn) are formed of PLLA, the surface of the first piezoelectric fiber 31 alone becomes negative and the inside thereof becomes positive when a tension is applied thereto. The surface of the second piezoelectric fiber 32 alone becomes positive and the inside thereof becomes negative when a tension is applied thereto.

Here, when the first piezoelectric fiber 31 of the S yarn and the second piezoelectric fiber 32 of the Z yarn are brought close to each other, a relatively strong electric field can be produced between the first piezoelectric fiber 31 and the second piezoelectric fiber 32. For example, the center portion of the Z yarn has a negative potential and the center portion of the S yarn has a positive potential so that the close portions (surfaces) have the same potential. In this case, the portion where the first piezoelectric fiber 31 and the second piezoelectric fiber 32 are close to each other has 0 V, and the positive potential at the inside of the first piezoelectric fiber 31 is further increased so as to keep the original potential difference. Similarly, the negative potential at the inside of the second piezoelectric fiber 32 is further lowered.

The cross section of the first piezoelectric fiber 31 primarily forms an electric field outward from the center and the cross section of the second piezoelectric fiber 32 primarily forms an electric field inward from the center. In the case where the first piezoelectric fiber 31 and the second piezoelectric fiber 32 are brought close to each other, these electric fields leak into the air to form an associated electric field, and an electric field circuit is formed between the first piezoelectric fiber 31 and the second piezoelectric fiber 32. That is, the potential difference at each point is defined by an electric field coupling circuit formed by complicatedly intertwining fibers, or a circuit formed by a current path which is accidentally formed in the yarn due to moisture or the like.

Figure 5A:
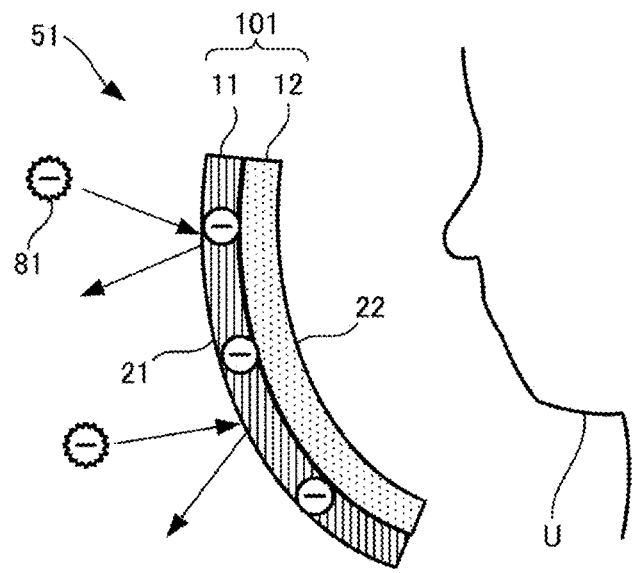
FIG. 5(A) is a schematic view showing a configuration of an antibacterial mask according to a first embodiment.
Figure 5B:
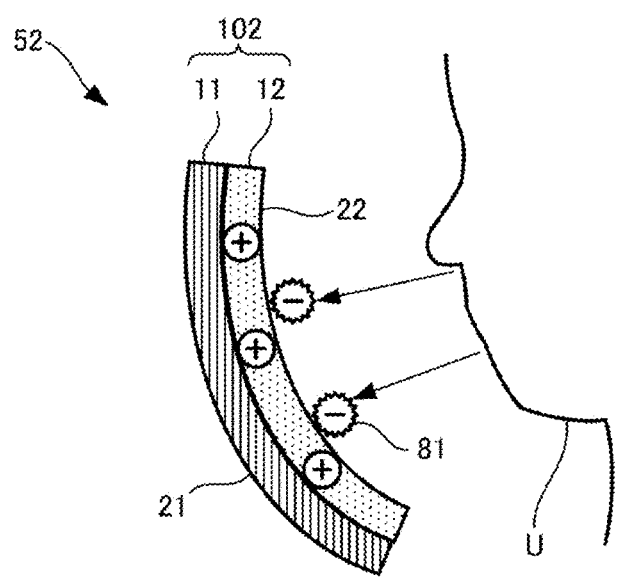
FIG. 5(B) is a schematic view showing a configuration of an antibacterial mask according to a second embodiment.

FIG. 5(A) is a schematic view showing a configuration of an antibacterial mask according to a first embodiment, and FIG. 5(B) is a schematic view showing a configuration of an antibacterial mask according to a second embodiment.

As shown in FIG. 5(A), an antibacterial mask 51 according to the first embodiment includes a filter 101. The drawing shows only a filter in the antibacterial mask, and the rest are omitted. The same applies to the descriptions of the second to sixth embodiments.

The filter 101 is formed, for example, in a rectangular shape so as to cover the mouth or nose of a human. The filter 101 includes a first principal surface 21 and a second principal surface 22 which is positioned opposite to the first principal surface 21. In the antibacterial mask 51, the second principal surface 22 is positioned on the side of a user U. The shape of the filter 101 is not limited to the rectangular shape, and may be a rhombus, a polygon, a circle, or an ellipse.

The filter 101 includes an outer layer 11 and an inner layer 12. The outer layer 11 is arranged on the side of the first principal surface 21, and the inner layer 12 is arranged on the side of the second principal surface 22. A plurality of first piezoelectric fibers 31 are arranged in the outer layer 11 on the side of the first principal surface 21. For example, the outer layer 11 includes a knitted fabric made by knitting the first piezoelectric fibers 31 as knitting yarns, a nonwoven fabric including the first piezoelectric fibers 31, or a woven fabric by weaving the first piezoelectric fibers 31.

The yarn constituting the filter 101 may include yarns other than the first piezoelectric fibers 31 that generate negative charges on their surfaces. By adjusting the amount of the first piezoelectric fibers 31, the ratio of the polarity of the electric charges to be generated can be adjusted for a particular application. In general, a piezoelectric fiber is worse in texture than cotton or the like, so that when a user wears it, the skin may be irritated. For this reason, when the yarn (cotton, etc.) which does not generate an electric charge is partially used in the filter 101, the texture of the filter 101 is improved, and the irritation to the skin is reduced.

Since a piezoelectric body is used in the filter 101, an electric field can be produced by a piezoelectric effect. Therefore, no power supply is required, and an electric shock may not occur in the filter 101. The life of the piezoelectric body lasts longer than the antibacterial effect of chemicals or the like. Further, the piezoelectric body may cause an allergic reaction less than chemicals.

When the filter 101 is stretched in use, negative charges are generated on the surfaces of the first piezoelectric fibers 31 in the outer layer 11. When negatively charged germs and fungi 81 come close to the side of the first principal surface 21, the negative charges generated by the first piezoelectric fibers 31 rebound such germs and fungi 81. This can prevent the germs and fungi 81 from entering into the filter 101.

The entire filter 101 may be formed of the first piezoelectric fibers 31. The filter 101 may have a filter formed of the first piezoelectric fibers 31 added in a frame shape to the margin of the filter formed of an ordinary cloth. When the filter formed of the first piezoelectric fibers 31 is provided in a frame shape, the ordinary cloth positioned at the center thereof is likely to attract the germs and fungi 81. Thus, it is possible to prevent the germs and fungi 81 from being absorbed into a body by attracting the germs and fungi 81 that have not been rebounded by the first piezoelectric fibers 31 to the ordinary cloth.

The entire filter 101 may not be uniformly formed. For example, the fabric of the filter 101 is formed so as to have a coarse mesh at the center portion and a finer mesh toward the end thereof. In addition, the filter 101 may have the first piezoelectric fibers 31 partially arranged by combining an ordinary cloth with the first piezoelectric fibers 31 in a patchwork form.

In the case where the ordinary cloth is combined with the filter 101, a negative charge generated from the entire filter 101 becomes smaller, as compared with the case where the entire filter 101 is formed of the first piezoelectric fibers 31, so that the effect of rebounding the germs and fungi 81 becomes weak. However, the first piezoelectric fibers 31 may rebound the germs and fungi 81 before the ordinary cloth attracts them, so that a certain degree of antibacterial effect can be exerted. In addition, in the case where the ordinary cloth is combined with the filter 101, not only the antibacterial effect but also air permeability can be ensured because the ordinary cloth is excellent in hygroscopicity.

In the case where the ordinary cloth is combined with the filter 101, the ratio of the ordinary cloth to the first piezoelectric fibers 31 is preferably 2:8 to 8:2 in terms of an area ratio. When the filter 101 includes the ordinary cloth at a given ratio, it can attract the germs and fungi 81 at a certain extent and can ensure air permeability. Further, when the filter 101 includes the first piezoelectric fibers 31 at a given ratio, it can sufficiently rebound the germs and fungi 81.

The shape of the antibacterial mask 51 is not limited to a general mask shape that covers a mouth or nose of a human, and may be, for example, a shape that covers only a mouth of a human. This prevents the germs and fungi 81 from entering into the mouth. Further, since the filter 101 rebounds the germs and fungi 81 in the surroundings, it prevents the germs and fungi 81 around a nose from entering into the nose. Thus, the use of the antibacterial mask 51 having this shape allows the germs and fungi 81 to be prevented from entering into the mouth or nose, as well as allowing the user to easily breathe because the nose is exposed to the outside.

The first piezoelectric fibers 31 used in the filter 101 may include yarns that generate different quantities of electric charges. In the case where the germs and fungi 81 adhere to the filter 101, a potential difference is produced in the filter 101, and the potential difference thus produced can provide an antibacterial effect. The yarns that generate different quantities of electric charges may be the one obtained by combining yarns having the different number of times of twisting, the one obtained by combining yarns having the different number of times of twisting partially in a yarn, or the one obtained by combining both of them.

An antibacterial mask according to the second embodiment will be described hereinbelow. In the description of the antibacterial mask according to the second embodiment, only different points from the first embodiment will be described, and the description of similar points will be omitted.

As shown in FIG. 5(B), an antibacterial mask 52 according to the second embodiment includes a filter 102. The filter 102 includes the outer layer 11 and the inner layer 12. A plurality of second piezoelectric fibers 32 are arranged in the inner layer 12 on the side of the second principal surface 22.

When the filter 102 is stretched in use, positive charges are generated on the surfaces of the second piezoelectric fibers 32 in the inner layer 12. When negatively charged germs and fungi 81 that are discharged from the user U come close to the side of the second principal surface 22, the positive charges generated by the second piezoelectric fibers 32 attract such germs and fungi 81 to the inner layer 12. This can prevent the germs and fungi 81 discharged from the user U from being inhaled into or adhering to the user U again by respiratory or the like. Further, since the germs and fungi 81 are once attracted to the filter 102, the antibacterial effect can be effectively exerted on the germs and fungi 81 that are collected by the electric charge generated in the filter 102.

Further, the filter 102 can generate a positive charge only when stretched. It does not generate a positive charge when not used, for example, during storage. Therefore, since a positive charge is not generated during storage, it is possible to prevent unnecessary germs and fungi 81 from adhering to the filter 102.

The entire filter 102 may be formed of the second piezoelectric fibers 32. The filter 102 may have a filter formed of the second piezoelectric fibers 32 added in a frame shape to the margin of the filter formed of an ordinary cloth. When the filter formed of the second piezoelectric fibers 32 is provided in a frame shape, the ordinary cloth positioned at the center thereof is likely to attract the germs and fungi 81. Thus, it is possible to further prevent the germs and fungi 81 from being absorbed into a body by attracting the germs and fungi 81 that have not been successfully attracted by the second piezoelectric fibers 32 to the ordinary cloth.

In the case where the ordinary cloth is combined with the filter 102, a positive charge generated from the entire filter 102 becomes smaller, as compared with the case where the entire filter 102 is formed of the second piezoelectric fibers 32, so that the effect of attracting the germs and fungi 81 becomes weak. However, since the ordinary cloth is excellent in hygroscopicity, the combination of the ordinary cloth with the filter 102 allows air permeability to be ensured.

In the case where the ordinary cloth is combined with the filter 102, the ratio of the ordinary cloth to the second piezoelectric fibers 32 is preferably 2:8 to 8:2 in terms of an area ratio. When the filter 102 includes the ordinary cloth at a given ratio, it can ensure air permeability. Further, when the filter 102 includes the second piezoelectric fibers 32 at a given ratio, an effect of sufficiently attracting the germs and fungi 81 can also be obtained.

The antibacterial mask 52 may have a shape that covers only a mouth of a human. The antibacterial mask 52 attracts the germs and fungi 81 spread from the mouth of the human, thereby preventing the germs and fungi 81 from reentering into the mouth. Further, since the filter 102 attracts the germs and fungi 81 in the surroundings, it prevents the germs and fungi 81 around a nose from entering into the nose. Thus, the use of the antibacterial mask 52 having this shape allows the germs and fungi 81 to be prevented from entering into the mouth or nose, as well as allowing the user to easily breathe because the nose is exposed to the outside.

The second piezoelectric fibers 32 used in the filter 102 may include yarns that generate different quantities of electric charges. In the case where the germs and fungi 81 adhere to the filter 102, a potential difference is produced in the filter 102, and the potential difference thus produced can provide an antibacterial effect. The yarns that generate different quantities of electric charges may be the one obtained by combining yarns having the different number of times of twisting, the one obtained by combining yarns having the different number of times of twisting partially in a yarn, or the one obtained by combining both of them.

Figure 6:
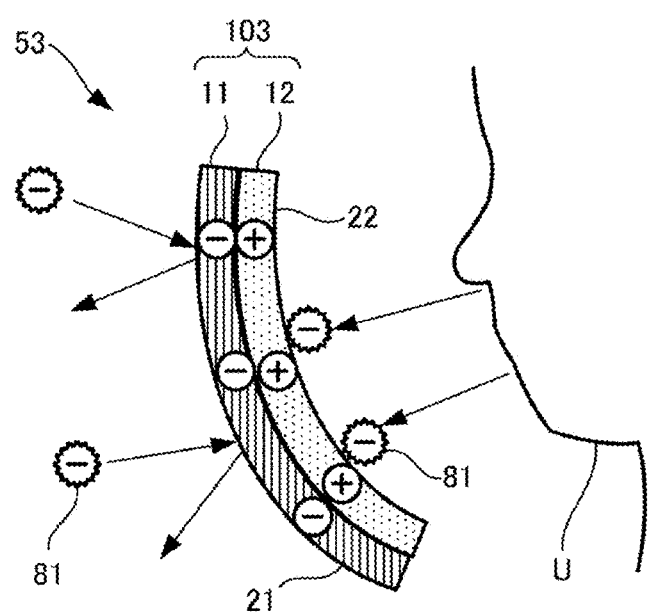
FIG. 6 is a schematic view showing a configuration of an antibacterial mask according to a third embodiment.

An antibacterial mask according to the third embodiment will be described hereinbelow. FIG. 6 is a schematic view showing a configuration of an antibacterial mask according to the third embodiment. In the description of the antibacterial mask 53 according to the third embodiment, only different points from the first embodiment will be described, and the description of similar points will be omitted.

As shown in FIG. 6, an antibacterial mask 53 according to the third embodiment includes a filter 103. The filter 103 includes the outer layer 11 and the inner layer 12. A plurality of first piezoelectric fibers 31 are arranged in the outer layer 11 on the side of the first principal surface 21. A plurality of second piezoelectric fibers 32 are arranged in the inner layer 12 on the side of the second principal surface 22.

When the filter 103 is stretched in use, positive charges are generated on the surfaces of the second piezoelectric fibers 32 in the inner layer 12. This can prevent the germs and fungi 81 discharged from the user U from being inhaled into or adhering to the user U again by respiratory or the like. Further, since the germs and fungi 81 are once attracted to the filter 103, the antibacterial effect can be effectively exerted on the germs and fungi 81 that are collected by the electric charge generated in the filter 103.

At the same time, when the filter 103 is stretched, negative charges are generated on the surfaces of the first piezoelectric fibers 31 in the outer layer 11. This can prevent the germs and fungi 81 from entering into the filter 103.

The first piezoelectric fiber 31 and the second piezoelectric fiber 32 used in the filter 103, as well as the first piezoelectric fibers 31 used in the filter 101 or the second piezoelectric fibers 32 used in the filter 102, may include yarns that generate different quantities of electric charges.

Figure 7A:
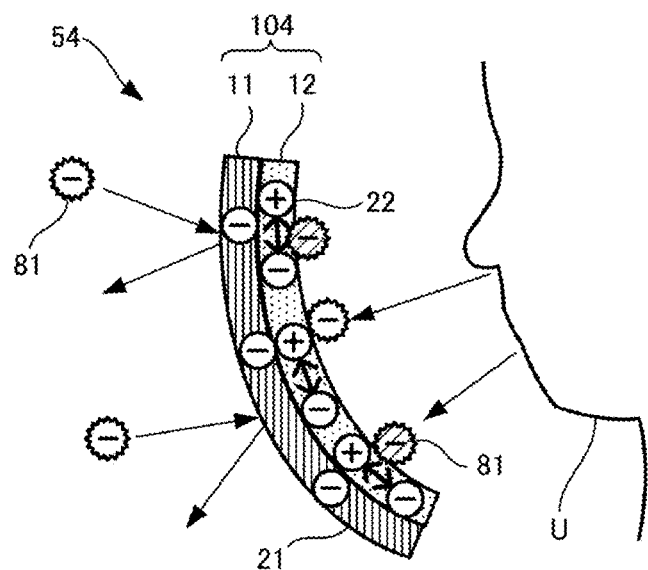
FIG. 7(A) is a schematic view showing a configuration of an antibacterial mask according to a fourth embodiment.
Figure 7B:
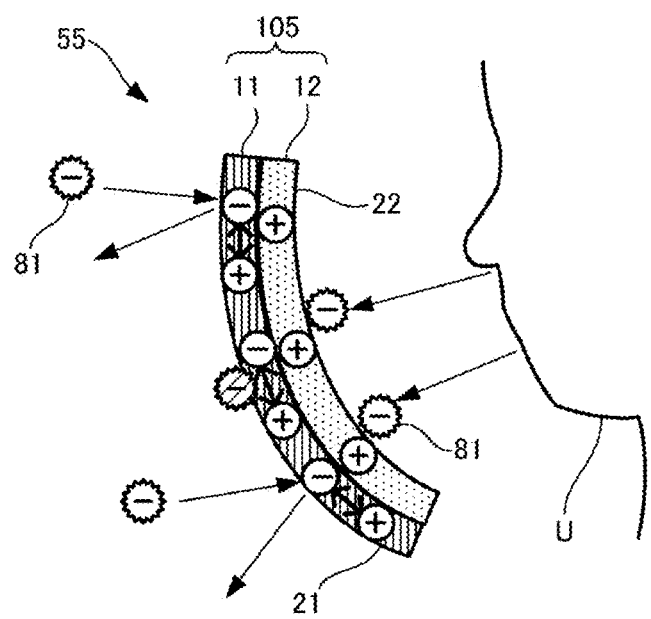
FIG. 7(B) is a schematic view showing a configuration of an antibacterial mask according to a fifth embodiment.

Antibacterial masks according to fourth and fifth embodiments will be described hereinbelow. FIG. 7(A) is a schematic view showing a configuration of an antibacterial mask according to the fourth embodiment, and FIG. 7(B) is a schematic view showing a configuration of an antibacterial mask according to the fifth embodiment. In the descriptions of the antibacterial masks according to the fourth and fifth embodiments, only different points from the third embodiment will be described, and the description of similar points will be omitted.

As shown in FIG. 7(A), an antibacterial mask 54 according to the fourth embodiment includes a filter 104. The filter 104 includes the outer layer 11 and the inner layer 12. A plurality of first piezoelectric fibers 31 are arranged in the outer layer 11 on the side of the first principal surface 21. A plurality of first piezoelectric fibers 31 and a plurality of second piezoelectric fibers 32 are arranged in the inner layer 12 on the side of the second principal surface 22.

When the filter 104 is stretched in use, positive charges are generated on the surfaces of the second piezoelectric fibers 32 in the inner layer 12. This can prevent the germs and fungi 81 discharged from the user U from being inhaled into or adhering to the user U again by respiratory or the like. At the same time, negative charges are generated on the surfaces of the first piezoelectric fibers 31 in the inner layer 12. Since both positive and negative charges are generated in the inner layer 12, a relatively large voltage generates between the first piezoelectric fiber 31 and the second piezoelectric fiber 32. Thus, the antibacterial effect can be further effectively exerted on the germs and fungi 81 that are attracted in the inner layer 12.

As shown in FIG. 7(B), an antibacterial mask 55 according to the fifth embodiment includes a filter 105. The filter 105 includes the outer layer 11 and the inner layer 12. A plurality of first piezoelectric fibers 31 and a plurality of second piezoelectric fibers 32 are arranged in the outer layer 11 on the side of the first principal surface 21. The plurality of second piezoelectric fibers 32 are arranged in the inner layer 12 on the side of the second principal surface 22.

When the filter 105 is stretched in use, negative charges are generated on the surfaces of the first piezoelectric fibers 31 in the outer layer 11. This can prevent the germs and fungi 81 from entering into the filter 105. At the same time, positive charges are generated on the surfaces of the second piezoelectric fibers 32 in the outer layer 11. Since both positive and negative charges are generated in the outer layer 11, a relatively large voltage generates between the first piezoelectric fiber 31 and the second piezoelectric fiber 32. Thus, the antibacterial effect can be further effectively exerted on the germs and fungi 81 that are left unrebounded in the outer layer 11. In addition, the antibacterial effect can be further effectively exerted on the germs and fungi 81 that are attracted in the inner layer 12.

Figure 8:
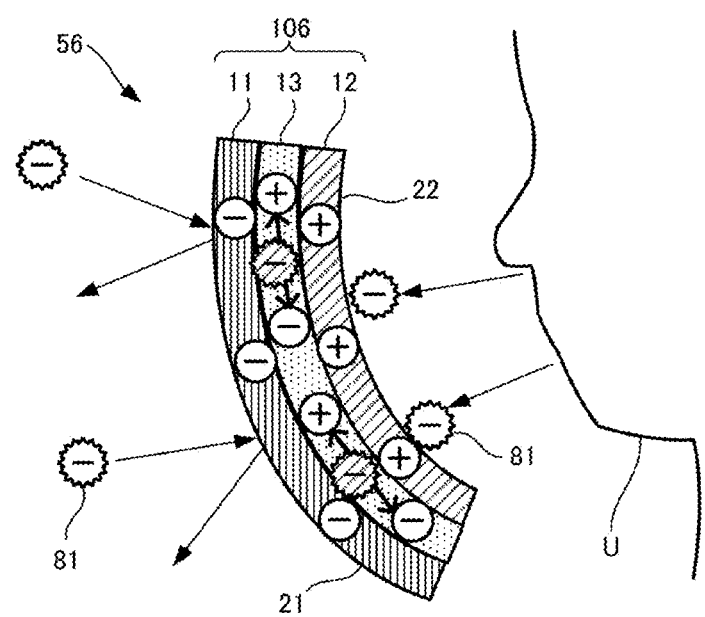
FIG. 8 is a schematic view showing a configuration of an antibacterial mask according to a sixth embodiment.

An antibacterial mask according to the sixth embodiment will be described hereinbelow. FIG. 8 is a schematic view showing a configuration of an antibacterial mask according to a sixth embodiment. In the description of the antibacterial mask according to the sixth embodiment, only different points from the third embodiment will be described, and the description of similar points will be omitted.

As shown in FIG. 8, an antibacterial mask 56 according to the sixth embodiment includes a filter 106. The filter 106 includes the outer layer 11, the inner layer 12, and an intermediate layer 13. The intermediate layer 13 is arranged between the outer layer 11 and the inner layer 12. A plurality of first piezoelectric fibers 31 and a plurality of second piezoelectric fibers 32 are arranged in the intermediate layer 13.

When the filter 106 is stretched in use, positive charges are generated on the surfaces of the second piezoelectric fibers 32 in the inner layer 12. In the inner layer 12, the positive charges generated by the second piezoelectric fibers 32 attract the germs and fungi 81 to the inner layer 12. Since both positive and negative charges are generated in the intermediate layer 13, a relatively large voltage generates between the first piezoelectric fiber 31 and the second piezoelectric fiber 32. Thus, the antibacterial effect can be further effectively exerted on the germs and fungi 81 that are attracted to the inner layer 12, or are left unrebounded in the outer layer 11.

The filters 101 to 106 as described above are applicable to products such as various clothes or medical members other than the mask. For example, the filters 101 to 106 can be applied to underwear (particularly, socks), towels, insoles for shoes, boots, and the like, the whole of sportswear, headwear, bedclothes (including futon, mattress, sheets, pillow, pillow cover, etc.), toothbrush, floss, filters for water purifier, air conditioner, or air purifier, stuffed toy, pet-related goods (mat for pets, pet clothing, inner for pet clothing), various mat products (for foot, hands, or toilet seats), curtain, kitchenware (sponge or dish towel), seats (seats for cars, electric cars, or airplanes), buffer member and facer for motorcycle helmets, sofa, bandage, gauze, suture, clothing for doctors and patients, supporter, sanitary supplies, sporting goods (inner materials for wear and gloves, or gloves used for material arts), or packaging materials.

Among clothes, in particular, socks (or supporters) are inevitably stretched along joints due to the movement by walking and the like. Therefore, the filters 101 to 106 generate electric charges at a high frequency. In addition, the socks absorb moisture such as sweat or the like to become a hotbed for growth of bacteria. The filters 101 to 106 are, however, capable of inhibiting the growth of bacteria and thus produces a remarkable effect as applications for measure against odor.

The filters 101 to 106 can also be used as a measure for inhibiting bacteria on body surfaces of animals except a human being. A cloth including a piezoelectric body is arranged so as to be opposed to at least a part of a skin of an animal, and an electric charge generated when an external force is applied to the piezoelectric body may inhibit the growth of bacteria on the animal body surface that is opposed to the cloth. Thus, it is possible to inhibit the growth of bacteria on the body surface of the animal and to treat ringworm on the body surface of the animal by a simple method which is higher in safety than chemicals or the like.

WO 2015/159832 A discloses a transducer which senses a displacement applied to a knitted or woven fabric using a plurality of piezoelectric yarns and conductive yarns. In this case, all the conductive yarns are connected to a detection circuit and a conductive yarn always pairs with a piezoelectric yarn. In WO 2015/159832 A, when an electric charge is generated in the piezoelectric yarn, an electron migrates from the conductive yarn to immediately neutralize the electric charge generated in the piezoelectric yarn. In WO 2015/159832 A, the detection circuit detects an electric current generated due to the migration of the electron and outputs the electric current as a signal. Accordingly, in this case, the generated potential is immediately canceled, so that no strong electric field is formed between the piezoelectric yarn and the conductive yarn, and the piezoelectric yarn and the piezoelectric yarn, which in turn no antibacterial effect is exerted.

Figure 9A:
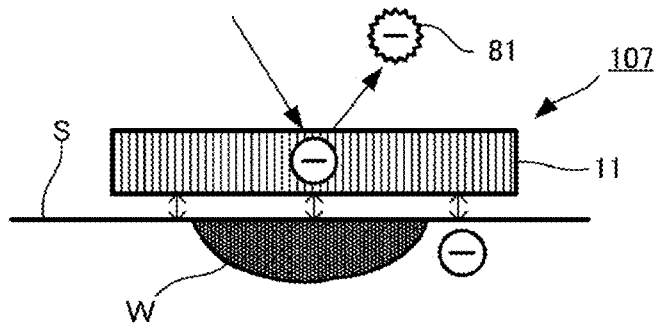
FIG. 9(A) is a schematic view showing a configuration of an antibacterial gauze according to a seventh embodiment.
Figure 9B:
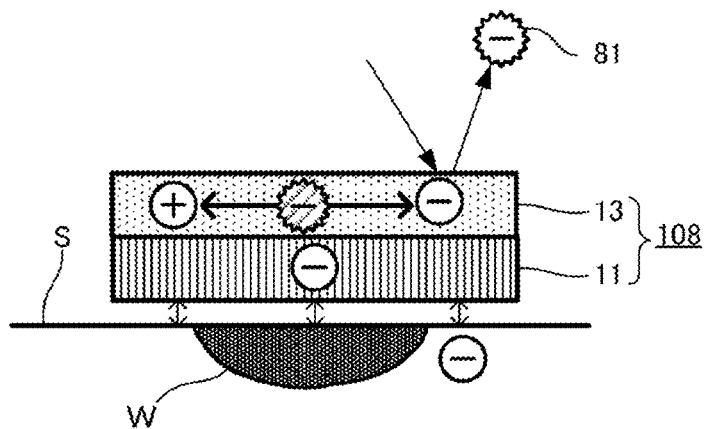
FIG. 9(B) is a schematic view showing a configuration of an antibacterial gauze according to an eighth embodiment.
Figure 9C:
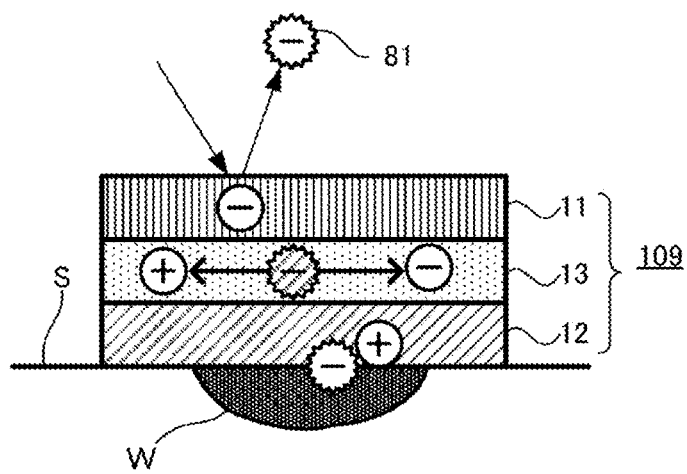
FIG. 9(C) is a schematic view showing a configuration of an antibacterial gauze according to a ninth embodiment.

Description will be made hereinbelow by exemplifying a gauze among the above-mentioned medical members. FIG. 9(A) is a schematic view showing a configuration of an antibacterial gauze according to a seventh embodiment, FIG. 9(B) is a schematic view showing a configuration of an antibacterial gauze according to an eighth embodiment, and FIG. 9(C) is a schematic view showing a configuration of an antibacterial gauze according to a ninth embodiment. FIGS. 9 (A) to 9 (C) show a main configuration alone. In the descriptions of the antibacterial gauzes according to the eighth and ninth embodiments, description relating to the similar configuration to the seventh embodiment will not be provided.

As shown in FIG. 9(A), an antibacterial gauze 107 according to the seventh embodiment is, for example, an adhesive plaster or the like to be applied to a wound W in a skin S. The antibacterial gauze 107, as well as the filter 101, includes the outer layer 11.

When the antibacterial gauze 107 is stretched in use, negative charges are generated on the surfaces of the first piezoelectric fibers 31 in the outer layer 11. This allows the germs and fungi 81 to be rebounded in the outer layer 11. An animal cell of the skin S is negatively charged. The negative charges generated when the first piezoelectric fibers 31 in the outer layer 11 are stretched and the negative charge that the animal cell of the skin S carries repel one another. Therefore, the animal cell of the skin S is less likely to be attached to the antibacterial gauze 107. The antibacterial gauze 107 is less likely to touch the wound W in the skin S to improve air permeability, so that wound healing can be hastened. In addition, the electric charges generated by the first piezoelectric fibers 31 stimulate the cell, which can thereby further hasten wound healing.

As shown in FIG. 9(B), an antibacterial gauze 108 according to the eighth embodiment has the intermediate layer 13 further laminated on the antibacterial gauze 107 on the outside. The intermediate layer 13 includes the first piezoelectric fibers 31 and the second piezoelectric fibers 32.

Since both positive and negative charges are generated in the intermediate layer 13, a relatively large voltage generates between the first piezoelectric fiber 31 and the second piezoelectric fiber 32. Thus, the antibacterial effect can be effectively exerted on the germs and fungi 81 that are left unrebounded in the outer layer 11 because of blood or body fluids adhering to the antibacterial gauze 108. This can rebound the germs and the fungi 81, and can also inhibit the growth of bacteria.

As shown in FIG. 9(C), an antibacterial gauze 109 according to the ninth embodiment, as well as the filter 106, includes the outer layer 11, the inner layer 12, and the intermediate layer 13. The inner layer 12 includes the second piezoelectric fibers 32.

When the antibacterial gauze 109 is stretched in use, positive charges are generated on the surfaces of the second piezoelectric fibers 32 in the inner layer 12. The positive charges generated by the second piezoelectric fibers 32 in the inner layer 12 and the negative charge that the animal cell of the skin S carries attract one another. Therefore, the animal cell of the skin S comes in close contact with the antibacterial gauze 109. This relatively blocks air permeability, so that the affected area which is not desirable to dry can be remedied. In addition, the electric charges generated by the second piezoelectric fibers 32 stimulate the cell, which can thereby further hasten wound healing.

The filters 101 to 106 according to this embodiment have the following applications, in addition to the bacteria countermeasure application.

(1) Biologically Acting Piezoelectric Fiber Products

Many tissues constituting a living body have piezoelectric properties. For example, collagen that constitutes a human body is a kind of protein, and is contained in a blood vessel, dermis, a ligament, tendon, bones, or cartilage in a large amount. Collagen is a piezoelectric body, and a collagen-oriented tissue may exhibit extremely large piezoelectric properties. Many reports about piezoelectric properties of bones have already been made (see, for example, "Seitai Kobunshino Atsudenki (Piezoelectricity of biopolymers)", Polymer vol. 16 (1967) No. 9, p. 795-800 written by Eiichi FUKADA). Therefore, a filter including the first piezoelectric fibers 31 or the second piezoelectric fibers 32 produces an electric field, and when the electric field alternates or the strength of the electric field varies, the piezoelectric body of the living body vibrates by inverse piezoelectric effect. A minute vibration is applied to a portion of the living body, for example, capillary or dermis, due to the alternating electric field produced by the first piezoelectric fibers 31 and/or the second piezoelectric fibers 32, or due to the variation in the strength of the electric field, so that the improvement of blood flow in the portion can be encouraged. This may accelerate the healing of a skin disorder or wound. Therefore, the filters 101 to 106 serve as biologically acting piezoelectric fiber products.

(2) Piezoelectric Fiber Products for Attracting Substance

As described above, the first piezoelectric fibers 31 generate negative charges when an external force is applied thereto. The second piezoelectric fibers 32 generate positive charges when an external force is applied thereto. Therefore, the first piezoelectric fibers 31 attract a substance having a positive charge (e.g., particles such as pollen) and the second piezoelectric fibers 32 attract a substance having a negative charge (e.g., harmful substances such as yellow dust). Accordingly, in the case where the filters 103 to 106 including the first piezoelectric fiber 31 and the second piezoelectric fiber 32 are applied to, for example, medical articles such as a mask, or filters for air-conditioning devices such as an air conditioner or an air purifier, they can attract fine particles such as pollen and yellow dust. Description will be made hereinbelow by way of examples.

Figure 10A:
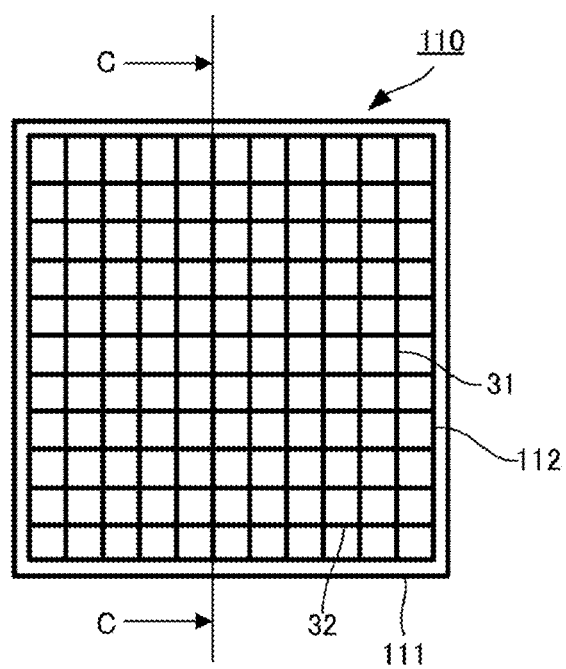
FIG. 10(A) is a schematic view of a filter according to a tenth embodiment.
Figure 10B:
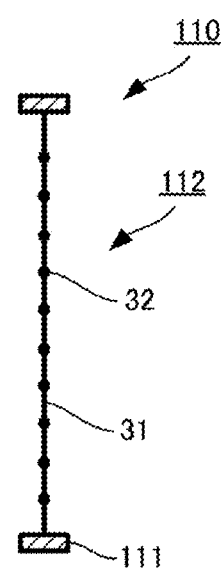
FIGS. 10(B) and 10(C) are cut end views taken along the line C-C in FIG. 10(A).
Figure 10C:
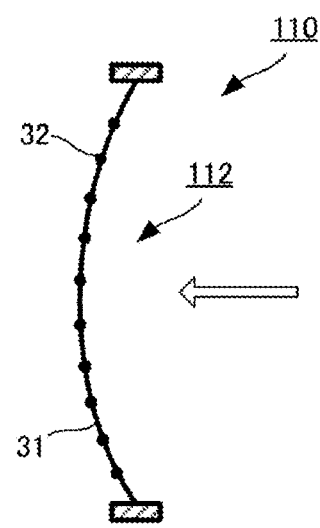

FIG. 10(A) is a schematic view of a filter according to a tenth embodiment. FIGS. 10(B) and 10(C) are cut end views taken along the line C-C in FIG. 10(A). FIGS. 11(A) to 11(D) are schematic views showing configurations of the filter according to the tenth embodiment, and are views for describing the variations in the filter. In the description of the filter according to the tenth embodiment, description relating to the similar configuration to the above-mentioned embodiments will not be provided. FIGS. 10(A) to 10(C) show only a frame member 111 that constitutes a filter, the first piezoelectric fibers 31, and the second piezoelectric fibers 32, and the configuration that constitutes the other filter of ordinary yarns or the like is omitted. The frame member 111 is an example of the "holding member" in the present invention.

A filter 110 according to the tenth embodiment is used as a filter for an air conditioner or an air purifier, for example. As shown in FIG. 10(A), the filter 110 includes the frame member 111 and a filter portion 112. The filter portion 112 is fixed to the frame member 111.

The filter portion 112 is a woven fabric or a nonwoven fabric including the first piezoelectric fibers 31 or the second piezoelectric fibers 32. For example, a portion of the warps that constitute the filter portion 112 is the first piezoelectric fibers 31 and a portion of the wefts that constitute the filter portion 112 is the second piezoelectric fibers 32. Here, for convenience of description, a filter constituted so as to principally generate a positive charge during nonuse and so as to principally generate a negative charge when extended will be described as the filter portion 112. In the filter portion 112, only the quantity of either positive charge or negative charge may vary.

Figure 11A:
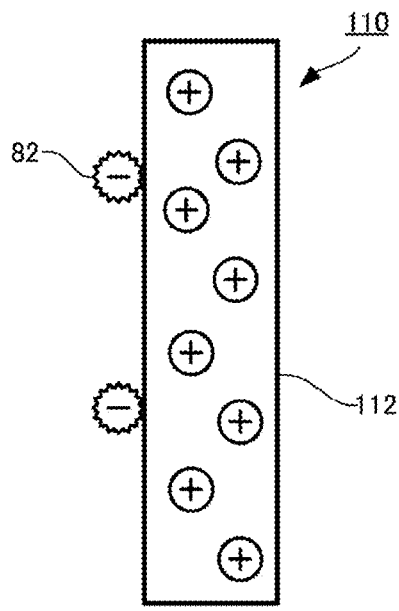
FIGS. 11(A) to 11(D) are schematic views showing configurations of the filter according to the tenth embodiment.

As shown in FIG. 10(B), the filter portion 112 maintains a flat shape during nonuse. During nonuse, the filter portion 112 may be fixed to a fixing member such as the frame member 111 while a tension is applied in the weft direction. That is, the filter portion 112 is fixed to a fixing member such as the frame member 111 while the second piezoelectric fibers 32 are in an extended state. In this case, for example, as shown in FIG. 11(A), the filter portion 112 in use is easily applied with tension and can generate a positive charge.

When the filter portion 112 in use is exposed to wind in the direction indicated by the arrow, it vibrates while being deformed as shown in FIG. 10(C). The vibration of the filter portion 112 refers to repetition of the state shown in FIG. 10(C) and the state shown in FIG. 10(B).

Figure 11B:
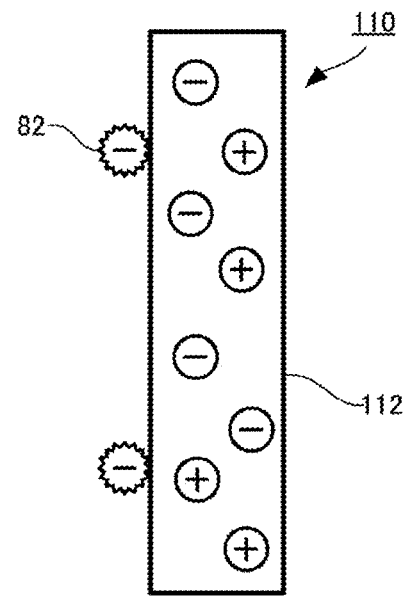

When the filter portion 112 vibrates, the first piezoelectric fibers 31 and the second piezoelectric fibers 32 of the filter portion 112 are stretched. At this time, in particular, the first piezoelectric fibers 31 of the warps are largely stretched, so that a negative charge is likely to be generated. Therefore, when the filter portion 112 is deformed, a negative charge is generated in the filter portion 112 as shown in FIG. 11(B), for example. This weakens an attraction force between dust 82 once attracted on the surface side and the filter portion 112. Accordingly, the dust 82 attracted to the filter portion 112 easily moves in the filter portion 112. The filter portion 112 in use vibrates while being continuously deformed, so that the condition of generating electric charge continues to vary.

Figure 11C:
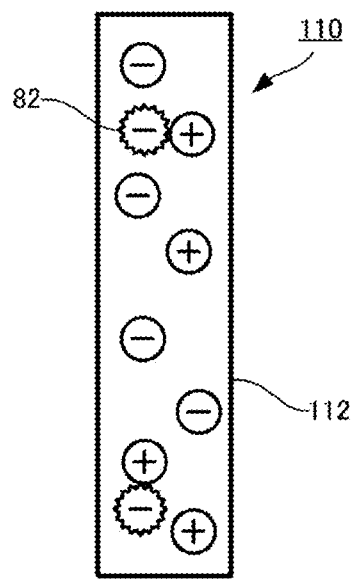
Figure 11D:
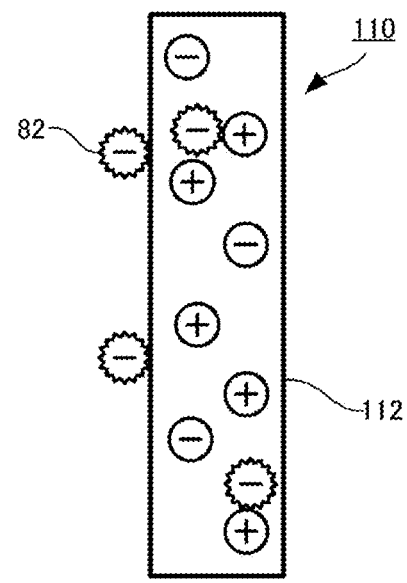

Here, in the case where there is a positive charge on the inner side of the filter portion 112, the dust 82 is pulled to the inner side as shown in FIG. 11(C). Thus, the filter portion 112 holds the dust 82 inside and vibrates, to thereby allowing the filter portion 112 to further generate a positive charge on its surface. Therefore, as shown in FIG. 11(D), the filter portion 112 can further attract the dust 82 on its surface. Thus, the filter portion 112 can exert an attraction force longer by vibration.

The filter portion 112 preferably has a structure in which the mesh becomes coarser toward the surface of the filter portion 112, and the mesh becomes finer toward the inside thereof. The filter 110 attracts the dust 82 on the surface of the filter portion 112. Thereafter, the dust 82 attracted to the surface moves as the filter portion 112 moves or as the condition of generating electric charge varies. At this time, when the surface of the filter portion 112 is coarse, the dust 82 is likely to enter into the filter portion 112. Therefore, the filter portion 112 is likely to absorb the dust 82 once captured on the surface of the filter portion 112 into the filter portion 112. Conversely, the filter portion 112 allows the dust 82 once absorbed into the filter portion 112 to be hardly flown outside the filter portion 112. Thus, the filter portion 112 can enhance the effect of holding the dust 82.

In FIGS. 10(A) to 10(C), the first piezoelectric fibers 31 of the wefts generate negative charges during extension, and the second piezoelectric fibers 32 of the warps generate positive charges during extension. However, the second piezoelectric fibers 32 may be used as wefts and the first piezoelectric fibers 31 may be used as warps. For example, in the case of using the first piezoelectric fibers 31 as both warps and wefts, negative charges are generated during extension, and in the case of using the second piezoelectric fibers 32 as both warps and wefts, positive charges are generated during extension.

Figure 12A:
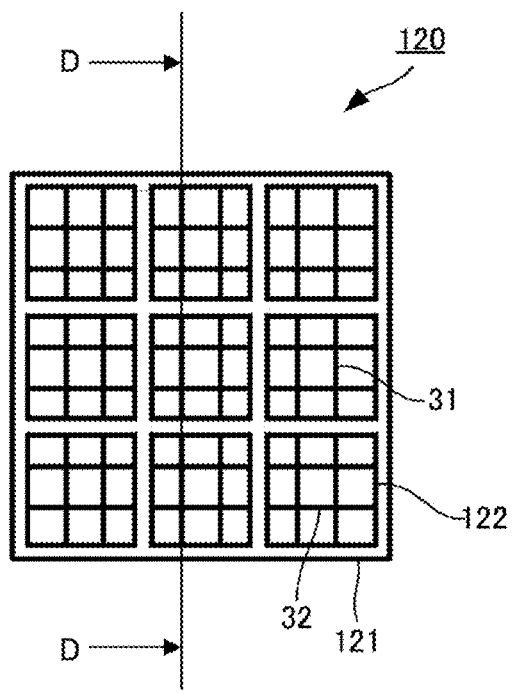
FIG. 12(A) is a schematic view of a modification 1 of the filter according to the tenth embodiment.
Figure 12B:
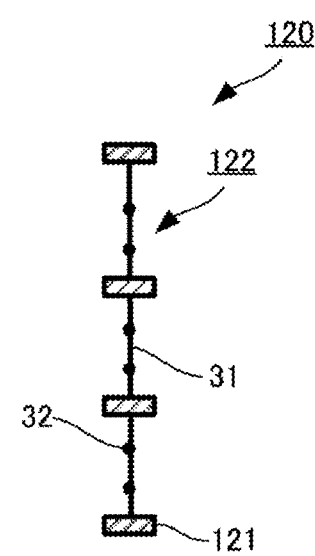
FIGS. 12(B) and 12(C) are cut end views taken along the line D-D in FIG. 12(A).
Figure 12C:
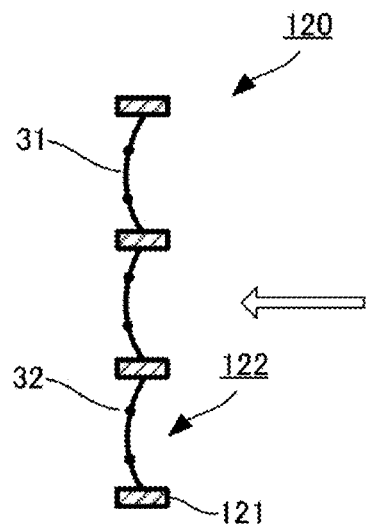
Figure 13A:
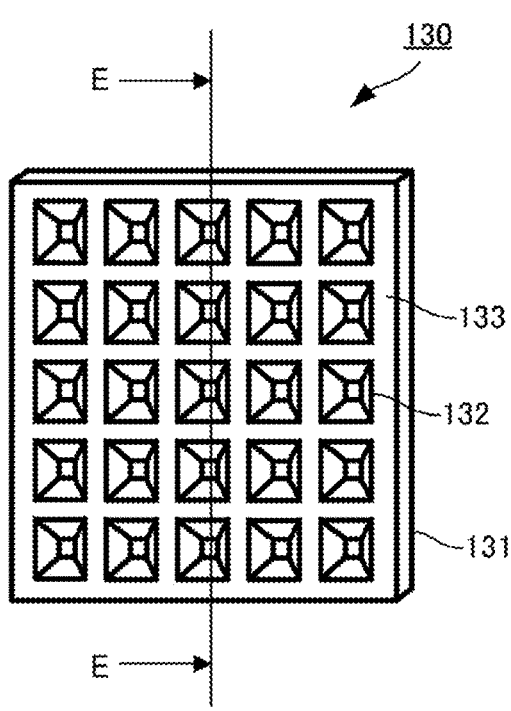
FIG. 13(A) is a schematic view of a modification 2 of the filter according to the tenth embodiment.
Figure 13B:
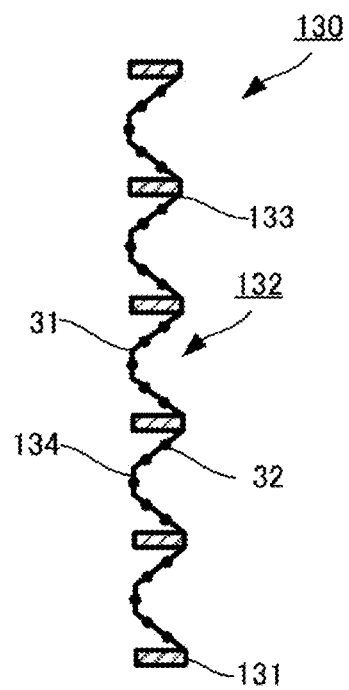
FIGS. 13(B) and 13(C) are cut end views taken along the line E-E in FIG. 13(A).
Figure 13C:
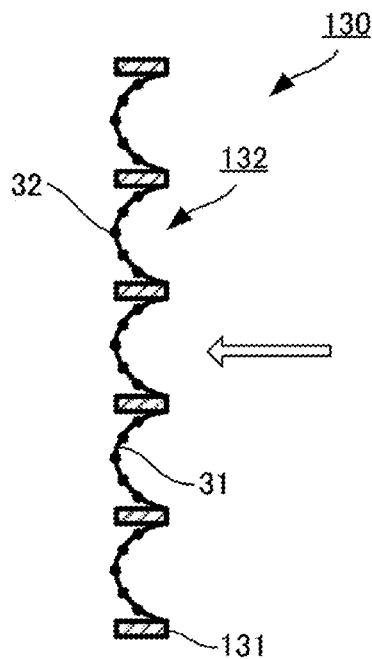
Figure 14A:
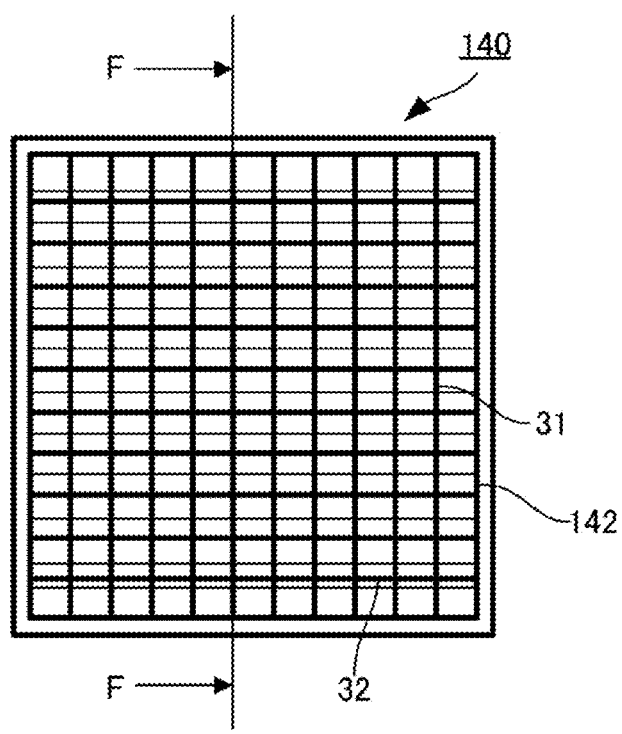
FIG. 14(A) is a schematic view of a modification 3 of the filter according to the tenth embodiment.
Figure 14B:
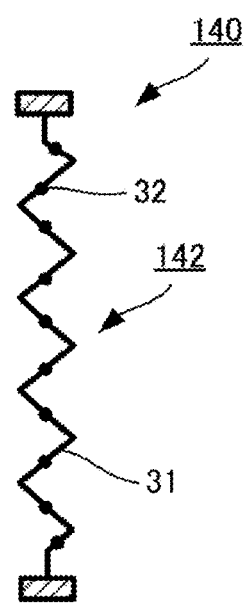
FIGS. 14(B) and 14(C) are cut end views taken along the line F-F in FIG. 14(A).
Figure 14C:
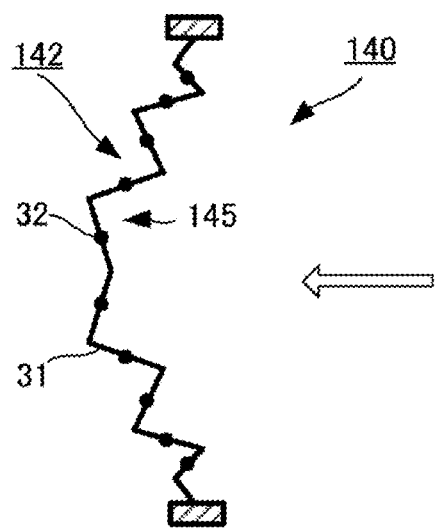

Next, modifications 1 to 3 of the filter 110 according to the tenth embodiment will be described hereinbelow. FIG. 12(A) is a schematic view of a modification 1 of the filter according to the tenth embodiment, and FIGS. 12(B) and 12(C) are cut end views taken along the line D-D in FIG. 12(A). FIG. 13(A) is a schematic view of a modification 2 of the filter according to the tenth embodiment, and FIGS. 13(B) and 13(C) are cut end views taken along the line E-E in FIG. 13(A). FIG. 14(A) is a schematic view of a modification 3 of the filter according to the tenth embodiment, and FIGS. 14(B) and 14(C) are cut end views taken along the line F-F in FIG. 14(A). In modifications 1 to 3, only different points from the filter 110 according to the tenth embodiment will be described, and the other description will be omitted.

As shown in FIGS. 12(A) and 12(B), a filter 120 according to modification 1 includes a frame member 121 having a different shape from the frame member 111. The frame member 121 is formed in a lattice shape. A filter portion 122 is fixed to the frame member 121. Therefore, the first piezoelectric fibers 31 and the second piezoelectric fibers 32 are fixed to the frame member 121 while being divided into small sections. The frame member 121 is an example of the "holding member" in the present invention.

As shown in FIG. 12(C), when the filter 122 in use is exposed to wind in the direction indicated by the arrow, it vibrates while being deformed. In the case where the frame member 121 is formed of a material that is less likely to be stretched as compared with the filter portion 122, the filter portion 122 vibrates in each section divided by the frame member 121. Thus, the filter portion 122 is entirely uniformly stretched as compared with the filter portion 112.

In the case of forming the frame member 121 into a lattice shape having uniform sections, the filter portion 122 in each lattice section is more uniformly stretched. Therefore, electric charge uniformly generates in the entire filter portion 122. This allows the filter 120 to uniformly absorb the dust 82 at the filter portion 122. Therefore, the filter 120 can prevent a part of the filter portion 122 from clogging. It is possible to properly provide the filter 120 with a strength suitable for use condition by changing the material or size of the frame member 121.

As shown in FIG. 13(A), a filter 130 according to modification 2 includes a frame member 131 having a lattice shape as in modification 1 and a filter portion 132 having a different shape. As shown in FIGS. 13(A) and 13(B), the filter portion 132 is three-dimensionally formed so as to protrude from one principal surface 133 of the filter 130 toward the other principal surface 134 thereof. Since the surface area of the filter portion 132 is three-dimensionally formed, it is large as compared with the filter portion 122 in modification 1. The frame member 131 is an example of the "holding member" in the present invention.

As shown in FIG. 13(C), when the filter 132 is exposed to wind in the direction indicated by the arrow, it vibrates while being deformed. At this time, since the surface area of the filter portion 132 is large, the filter 130 can attract and hold more dust 82 than the filter 120.

As shown in FIG. 14(A), a filter 140 according to modification 3 includes a filter portion 142 having a different shape from the filter 110. The filter portion 142 is formed in a bellows shape as shown in FIGS. 14(A) and 14(B). Therefore, since the surface area of the filter portion 140 is largely formed, the filter 140 can attract and hold more dust 82.

As shown in FIG. 14(C), when the filter 142 in use is exposed to wind in the direction indicated by the arrow, it vibrates while being deformed. At this time, since the filter portion 142 is formed in a bellows shape, the movement becomes large as compared with the case of forming the filter in a flat shape like the filter 110. Thus, the filter 140 can generate larger electric charge than the filter 110. That is, the filter 140 has a higher force of attracting the dust 82 as compared with the filter 110. Accordingly, the filter 140 attracts and holds the dust 82 more quickly than the filter 110.

Further, since the filter portion 142 is formed in a bellows shape, vibration occurs also in a direction different from the direction indicated by the arrow as shown in FIG. 14(C). For example, the filter portion 142 generates vibration in a direction perpendicular to the arrow shown in FIG. 14(C) by spirally moving air at a portion 145 recessed from the wind receiving side in the filter portion 142. Thus, the filter portion 142 performs a more complicated movement, so that the occurrence of electric charge in the filter portion 142 becomes more complicated. Therefore, the filter 140 is more likely to absorb the dust 82 that has been once captured on the surface of the filter portion 142, into the filter portion 142.

Figure 15:
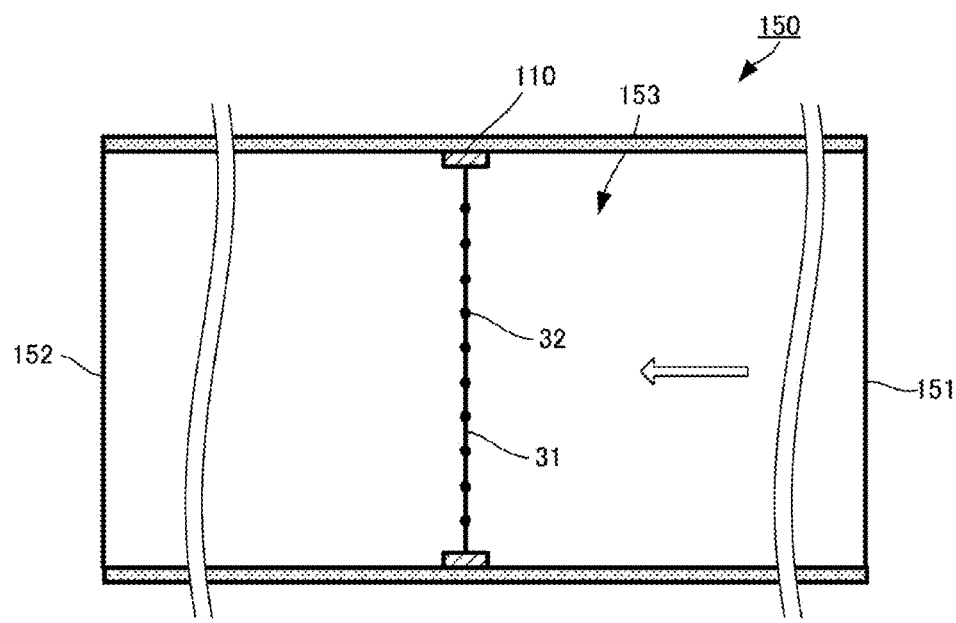
FIG. 15 is a schematic view showing a case where a filter is used in an air-conditioning device.

FIG. 15 is a schematic view showing a case where a filter is used in an air-conditioning device. In FIG. 15, a case of using the filter 110 will be described as an example. An air-conditioning device 150 includes an inlet port 151, an exhaust port 152, and a communicating passage 153 that communicates between the inlet port 151 and the exhaust port 152. The filter 110 is arranged in the communicating passage 153, for example. Accordingly, it is possible to attract fine particles such as pollen or yellow dust in the air that circulates in the communicating passage 153.

A configuration in which an electrical conductor is used in a core yarn, an insulator is wound around the electrical conductor, and an electric current is flown into the electrical conductor to generate an electric charge is also a fiber that generates an electric charge. It should be noted that a piezoelectric body produces an electric field by a piezoelectric effect, so that no power supply is required, and an electric shock may not occur. The life of the piezoelectric body lasts longer than the antibacterial effect of chemicals or the like. Further, the piezoelectric body may cause an allergic reaction less than chemicals. In recent years, exhibition of resistant bacteria due to chemicals, particularly, antibiotics has been a major problem. However, the sterilization method according to the present invention is not considered to generate resistant bacteria in terms of its mechanism.

As the fiber that generates a negative electric charge on its surface, a Z yarn using PDLA, as well as an S yarn using PLLA, is considered. In addition, as the fiber that generates a positive electric charge on its surface, an S yarn using PDLA, as well as a Z yarn using PLLA, is considered.

The S yarn using PLLA as the fiber that generates a negative electric charge on its surface in stretching, and the Z yarn using PLLA as the fiber that generates a positive electric charge on its surface during stretching are exemplified, but they are not limited to these configuration. For example, instead of the first piezoelectric fiber 31, other fibers can be used as long as it generates a negative electric charge on its surface during stretching. Similarly, instead of the second piezoelectric fiber 32, other fibers can be used as long as it generates a positive electric charge on its surface during stretching. Conversely, a fiber that generates a positive or negative electric charge during shrinking can also be used.

Further, in the present embodiment, as long as a potential difference is produced between the first piezoelectric fibers 31 and the second piezoelectric fibers 32, an effect is obtained. Even if an electric charge of the same polarity generates in the first piezoelectric fiber 31 and the second piezoelectric fiber 32, a similar effect can be obtained as long as the amount of the electric charge generated in each of the piezoelectric fibers is different. For example, a combination of piezoelectric fibers having the different number of twists, a combination of piezoelectric fibers having the different number of filaments, a combination of piezoelectric fibers having different filament diameters, a combination of piezoelectric fibers having different piezoelectric constants, and a combination of piezoelectric fibers having these conditions combined are included.

The filter according to the present embodiment can be adopted to, for example, a screen door and the like, in addition to the above-mentioned embodiments. In the screen door, a mesh sheet including the filter is fixed to a frame in a tension applied state. In a normal state, the filter is maintained under tension. Accordingly, a tension is applied to the filter by a minute vibration generated by an external environment, so that an antibacterial effect or the like can be easily exerted.

Finally, the present embodiments should therefore be considered in all respects as illustrative and not restrictive. The scope of the invention is given by the appended claims, rather than the preceding embodiments. Further, all variations and equivalents which fall within the range of the claims are intended to be embraced therein.

DESCRIPTION OF REFERENCE SYMBOLS

21: First principal surface
22: Second principal surface
31: First piezoelectric fiber (right-twisted yarn: S yarn)
32: Second piezoelectric fiber (left-twisted yarn: Z yarn)
51, 52, 53, 54, 55, 56: Antibacterial mask
101, 102, 103, 104, 105, 106, 110, 120, 130, 140: Filter
107, 108, 109: Antibacterial gauze (filter)

The invention claimed is:

1. An antibacterial mask comprising:
a filter portion having a first principal surface and a second principal surface opposite the first principal surface, the filter portion including a plurality of first piezoelectric yarns that generate at least a first charge by stretching,
wherein the filter portion has a coarse mesh portion and a fine mesh portion.

2. The antibacterial mask according to claim 1, wherein the second principal surface is positioned on a user side of the antibacterial mask.

3. The antibacterial mask according to claim 2, wherein the filter portion includes an outer layer and an inner layer, the outer layer being arranged on a side of the first principal surface, and the inner layer being arranged on a side of the second principal surface.

4. The antibacterial mask according to claim 3, wherein the plurality of first piezoelectric yarns are arranged in the outer layer.

5. The antibacterial mask according to claim 3, wherein the plurality of first piezoelectric yarns are arranged in the inner layer.

6. The antibacterial mask according to claim 3, wherein the plurality of first piezoelectric yarns are arranged in the outer layer, and the antibacterial mask further comprises a plurality of second piezoelectric yarns that generate at least the first charge by stretching arranged in the inner layer.

7. The antibacterial mask according to claim 2, wherein the filter portion includes an outer layer, an inner layer, and an intermediate layer between the outer layer and the inner layer, the outer layer being arranged on a side of the first principal surface, and the inner layer being arranged on a side of the second principal surface.

8. The antibacterial mask according to claim 7, wherein the plurality of first piezoelectric yarns are arranged in the outer layer, and the antibacterial mask further comprises:

a plurality of second piezoelectric yarns that generate at least the first charge by stretching arranged in the inner layer; and a plurality of third piezoelectric yarns that generate at least the first charge by stretching arranged in the intermediate layer.

9. The antibacterial mask according to claim 1, wherein the filter portion is a knitted fabric containing the first piezoelectric yarns.

10. The antibacterial mask according to claim 1, wherein the filter portion is a nonwoven fabric including the first piezoelectric yarns.

11. The antibacterial mask according to claim 1, wherein the filter portion is a woven fabric containing the first piezoelectric yarns.

12. The antibacterial mask according to claim 1, wherein the filter portion further includes a cloth that does not include piezoelectric yarns.

13. The antibacterial mask according to claim 12, wherein the first piezoelectric yarns and the cloth are arranged in a patchwork form.

14. The antibacterial mask according to claim 12, wherein a ratio of the cloth to the plurality of first piezoelectric yarns is 2:8 to 8:2.

15. The antibacterial mask according to claim 1, wherein the filter portion has a shape that covers only a mouth of a user.

16. The antibacterial mask according to claim 1, wherein the filter portion is shaped so as to cover a mouth or a nose of a user.

17. The antibacterial mask according to claim 1, wherein the filter portion is shaped so as to cover a mouth and a nose of a user.

18. The antibacterial mask according to claim 1, wherein the plurality of first piezoelectric yarns are arranged into a plurality of first piezoelectric fibers, each of the plurality of first piezoelectric fibers containing a set of yarns of the plurality of first piezoelectric yarns.

19. An antibacterial mask comprising:

a filter portion having a first principal surface and a second principal surface opposite the first principal surface, the filter portion including a plurality of first piezoelectric yarns that generate at least a first charge by stretching, wherein the entire filter portion is formed of the first piezoelectric yarns.

20. The antibacterial mask according to claim 19, wherein the second principal surface is positioned on a user side of the antibacterial mask.

21. The antibacterial mask according to claim 20, wherein the filter portion includes an outer layer and an inner layer, the outer layer being arranged on a side of the first principal surface, and the inner layer being arranged on a side of the second principal surface.

22. The antibacterial mask according to claim 20, wherein the filter portion includes an outer layer, an inner layer, and an intermediate layer between the outer layer and the inner layer, the outer layer being arranged on a side of the first principal surface, and the inner layer being arranged on a side of the second principal surface.

23. The antibacterial mask according to claim 19, wherein the filter portion is a knitted fabric.

24. The antibacterial mask according to claim 19, wherein the filter portion is a nonwoven fabric.

25. The antibacterial mask according to claim 19, wherein the filter portion is a woven fabric.

26. The antibacterial mask according to claim 19, wherein the antibacterial mask further includes a cloth that does not include piezoelectric yarns.

27. The antibacterial mask according to claim 19, wherein the filter portion has a shape that covers only a mouth of a user.

28. The antibacterial mask according to claim 19, wherein the filter portion is shaped so as to cover a mouth or a nose of a user.

29. The antibacterial mask according to claim 19, wherein the filter portion is shaped so as to cover a mouth and a nose of a user.

30. The antibacterial mask according to claim 19, wherein the plurality of first piezoelectric yarns are arranged into a plurality of first piezoelectric fibers, each of the plurality of first piezoelectric fibers containing a set of yarns of the plurality of first piezoelectric yarns.

* * * * *